US011934982B2

United States Patent
Srinivasan et al.

(10) Patent No.: US 11,934,982 B2
(45) Date of Patent: Mar. 19, 2024

(54) FEEDSTOCK PROCESSING CORROSION MANAGEMENT

(71) Applicant: Honeywell International Inc., Charlortte, NC (US)

(72) Inventors: Sridhar Srinivasan, Houston, TX (US); Kwei Meng Yap, Houston, TX (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 92 days.

(21) Appl. No.: 17/188,665

(22) Filed: Mar. 1, 2021

(65) Prior Publication Data

US 2021/0365860 A1     Nov. 25, 2021

Related U.S. Application Data

(60) Provisional application No. 63/028,667, filed on May 22, 2020.

(51) Int. Cl.
| | |
|---|---|
| *G06Q 10/0631* | (2023.01) |
| *G01N 33/28* | (2006.01) |
| *G06F 30/20* | (2020.01) |
| *G06Q 30/0201* | (2023.01) |

(52) U.S. Cl.
CPC ... *G06Q 10/06315* (2013.01); *G01N 33/2823* (2013.01); *G06F 30/20* (2020.01); *G06Q 30/0206* (2013.01)

(58) Field of Classification Search
None
See application file for complete search history.

(56) References Cited

U.S. PATENT DOCUMENTS

| | | | | |
|---|---|---|---|---|
| 9,103,813 | B2 * | 8/2015 | Kusinski | G01N 17/02 |
| 9,140,679 | B2 * | 9/2015 | Kusinski | G01N 33/2823 |
| 9,347,009 | B2 * | 5/2016 | Kusinski | C10L 1/04 |
| 9,464,242 | B2 * | 10/2016 | Kusinski | C10G 75/00 |
| 2005/0050009 | A1 | 3/2005 | Gardner et al. | |
| 2010/0100404 | A1 | 4/2010 | Poole et al. | |
| 2011/0264415 | A1 * | 10/2011 | Bleackley | G06F 30/13 |
| | | | | 703/1 |

(Continued)

OTHER PUBLICATIONS

Zeinalov et al., Petroleum acids and Corrosion, Petroleum Chemistry, 2009, vol. 49, No. 3. pp 185-192. (Year: 2009).*

(Continued)

*Primary Examiner* — Stephanie Z Delich
(74) *Attorney, Agent, or Firm* — Alston & Bird LLP (57) ABSTRACT

A computer implemented method includes obtaining, by the computer, assay data for a feedstock containing measurements for one or more aspects of the first feedstock, a first equipment model containing properties of processing units, and processing conditions containing one or more variables by which the first feedstock will be processed by the processing units. The computer determines a corrosion amount of the processing units using the processing conditions, the properties of the processing units contained in the equipment model, and the assay data for the feedstock, and stores/displays the corrosion amount of the processing units. A safety warning may be displayed, and the feedstock rejected if the corrosion amount exceeds a predetermined safety level for one or more of the processing units.

20 Claims, 7 Drawing Sheets

(56) References Cited

U.S. PATENT DOCUMENTS

| | | | |
|---|---|---|---|
| 2012/0160707 A1* | 6/2012 | Kusinski | G01N 33/2876 702/30 |
| 2016/0188769 A1* | 6/2016 | Aylott | G06Q 50/06 703/6 |
| 2016/0281607 A1* | 9/2016 | Asati | F02C 7/26 |
| 2019/0316902 A1* | 10/2019 | Sparago | G01B 21/08 |

OTHER PUBLICATIONS

IPEA/409—International Preliminary Report on Patentability dated Dec. 1, 2022 for WO Application No. PCT/US21/033342.
"International Application Serial No. PCT/US2021/033342, International Search Report dated Oct. 15, 2021", 4 pgs.
"International Application Serial No. PCT/US2021/033342, Written Opinion dated Oct. 15, 2021", 7 pgs.

* cited by examiner

| ANALYZE 320 | | 325 | 330 | CORROSION RATE 335 | DESIGN CR 340 | TEMPERATURE 345 | TOTAL SULFER 350 |
|---|---|---|---|---|---|---|---|
| | | TAG | | MPY | MPY | F | WT% |
| SR. NO. | UNIT | | ALLOY | | | | |
| 1 | FLASH DRUM FEED TRANSFER LINE | | CS | NA | NA | | |
| 2 | OUTLET OF FLASH DRUM | | CS | NA | NA | | |
| 3 | INLET OF CRUDE HEATER | | 316 L | NA | NA | | |
| 4 | OUTLET OF CRUDE HEATER | | 316 L | NA | NA | | |
| 5 | INLET OF CRUDE HEATER | | 316 L | NA | NA | | |
| 6 | OUTLET OF CRUDE HEATER | | 316 L | NA | NA | | |
| 7 | CDU FEED TRANSFER LINE | | 316 L | NA | NA | | |
| 8 | DUMMY DRAW-OFF LINE | | 5 CR | NA | NA | | |
| 9 | LC DRAW-OFF LINE | | 304 SS | NA | NA | | |
| 10 | DUMMY SIDECUT PIPING | | 12 CR | NA | NA | | |
| 11 | DUMMY SIDECUT PIPING | | 12 CR | NA | NA | | |
| 12 | HAGO SIDECUT PIPING | | 12 CR | NA | NA | | |
| 13 | LC SIDECUT PIPING | | 12 CR | NA | NA | | |
| CRUDE CORROSIVITY TOOL | | | | | | | |

FEEDSTOCK PROCESSING CORROSION MANAGEMENT

RELATED APPLICATIONS

This application claims priority to U.S. Provisional Application Ser. No. 63/028,667, filed May 22, 2020, which application is incorporated herein by reference in its entirety.

BACKGROUND

Processing equipment is used in many industries to process feedstock. One example feedstock is crude oil. Crude oil may arrive at an oil refinery via different carries, such as oil tanker ships and pipelines in the form of batches, referred to as opportunity crudes. Available batches may have different corrosive effects on processing equipment which may be estimated by very experienced operators. An operator of a refinery may have options to select which batches of feedstock to process based on those estimates. The estimates may be made based in part on data that describes certain characteristics of the feedstock, such as Total Acid Number (TAN) and Sulfur properties. Larger batches of oil that are estimated to corrode processing equipment faster may be accepted or avoided based on such estimates and further based on potential value of processing such batches. Such estimates, however, may vary in accuracy depending on operator experience and luck, leading to potentially dangerous events occurring based on processing a batch selected based on an inaccurate estimate.

SUMMARY

A computer implemented method includes obtaining, by the computer, assay data for a feedstock containing measurements for one or more aspects of the first feedstock-, a first equipment model containing properties of processing units, and processing conditions containing one or more variables by which the first feedstock will be processed by the processing units. The computer determines a corrosion amount of the processing units using the processing conditions, the properties of the processing units contained in the equipment model, and the assay data for the feedstock-, and stores/displays the first corrosion amount of the processing units. A safety warning may be displayed, and the feedstock rejected if the corrosion amount exceeds a predetermined safety level for one or more of the processing units.

Overall corrosion may be managed by iteratively determining equipment and processing unit corrosion amounts for various, disparate feedstock and selecting a feedstock to process based on one or more goals. Goals may include meeting safety concerns, minimizing corrosion, optimizing processing capabilities by selecting and blending various opportunity crude feedstocks, and balancing maximizing profit with minimizing corrosion.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

The functionality can be configured to perform an operation using, for instance, software, hardware, firmware, or the like. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware. The term, "logic" encompasses any functionality for performing a task. For instance, each operation illustrated in the flowcharts corresponds to logic for performing that operation. An operation can be performed using, software, hardware, firmware, or the like. The terms, "component," "system," and the like may refer to computer-related entities, hardware, and software in execution, firmware, or combination thereof. A component may be a process running on a processor, an object, an executable, a program, a function, a subroutine, a computer, or a combination of software and hardware. The term, "processor," may refer to a hardware component, such as a processing unit of a computer system.

Furthermore, the claimed subject matter may be implemented as a method, apparatus, or article of manufacture using standard programming and engineering techniques to produce software, firmware, hardware, or any combination thereof to control a computing device to implement the disclosed subject matter. The term, "article of manufacture," as used herein is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, among others. In contrast, computer-readable media, i.e., not storage media, may additionally include communication media such as transmission media for wireless signals and the like.

Refinery operators constantly have a need to quantify the corrosion effect of opportunity crudes and crude blends they process on reliability of crude unit equipment and operations. However, such quantification has been hitherto difficult because it requires the ability to incorporate and integrate crude blend corrosivity with process conditions, unit operating parameters and crude assay properties. A feedstock processing corrosion management system provides the ability to use crude assays, processing information, and corrosion prediction information to provide refinery operators the ability to automate corrosion quantification and optimization of crude blends and fractions to be used through crude unit processes and across entire crude units, enabling identification of potential corrosion hot spots and unit ability to safely utilize opportunity crudes and blended fractions.

Opportunity crudes and crude blends represent economic opportunity to refinery operators. However, many operators shy away from using opportunity crudes and blended fractions because the damage that the crude blend may cause to the crude unit equipment and piping is not known before the blend is processed. There are significant differences between crudes and blended fractions in terms of organic acid and Sulfur content. In addition, crude processing units can have hundreds of different pieces of equipment with different metals that may corrode at different rates under different processing conditions. While operators can attempt to estimate corrosion rates, such estimates may easily end up bearing little resemblance to actual corrosion rates.

A feedstock processing corrosion management system is used to provide a comprehensive corrosion and process correlated unit analysis to quantify corrosion rates and provide operators a process flow diagram driven corrosion map and hot spot identification for multiple different opportunity crudes and for multiple different processing units. The system enables an operator to select an opportunity crude to process as well as the processing unit to use on the selected crude based on quantified effects. Without the use of the system, operators usually default to conservatively selecting crudes, missing opportunities to optimize processing capabilities, profitability, and informed selectivity of crude opportunities.

The system utilizes large, disparate data sets that include feedstock assay data, processing equipment data, and process data to quantify and generate corrosion rates for hundreds of critical unit locations, correlating corrosion rates to blended crude TAN and Sulfur properties, as a precursor to ensuring that a given crude blend may be safely processed, ensuring pre-set corrosion rate limits for unit equipment piping and metallurgy.

The system can quantify predicted corrosion for hundreds of crude blends and processing units, leading to better processing decisions by refinery operators in utilizing cheaper feedstock in a safe and reliable manner.

The system enables automated evaluation of opportunity crudes and crude blends available through industry assay databases—to pictorially quantify corrosion across crude operating units.

Crude opportunities, including crude blends usually have an associated crude assay associated, such as a well known Haverly® crude assay. A crude oil assay is a chemical evaluation of crude oil feedstocks by petroleum testing laboratories. Each crude oil type has unique molecular and chemical characteristics. No two crude oil types are identical and there are crucial differences in crude oil quality. The results of crude oil assay testing provide extensive detailed hydrocarbon analysis data for refiners, oil traders and producers.

In one embodiment, crude assay data is converted to a format compatible with the system, such as an excel spreadsheet format. Multiple crude assays for various crude opportunities are converted and imported into the system for use by a corrosion rate prediction tool of the system. In addition, the system accesses models corresponding to multiple different processing units. The models specify metallurgical data for the multiple metals comprising the processing units, including piping system that transfer the oil between equipment in each unit. Process data for each unit is also accessed so that environmental parameters for processing each different crude opportunity in each different processing unit are available for use in calculating corrosion rates. Typical process data includes available environmental and operating factors such as pressure, temperature and stream information for each piece of equipment correlated with a process flow diagram for a processing unit. The processing data combined with the Naphthenic acid content and $H_2S$ level (active sulfur) data from crude assay is used by the system to calculate corrosion rates.

In one example, the system is used to select various crudes for processing to safely optimize processing unit utilization. The system may be used to monitor a 30-day rolling-average TAN envelope versus prior methods based on a 30-day fixed TAN envelope. The use of the rolling-average TAN envelope enables the tool to provide visibility into processing, enabling a refinery operator to purchase more economical crudes for processing. In some instances, a more economically beneficial crude may be processed in addition to several less corrosive crudes to safely stay within the TAN envelope, yet optimize utilization of processing units.

The system facilitates better management of corrosion rates for complex crude throughput, providing for continuous flexibility while maintaining rigorous reliability and mechanical integrity, providing crude corrosion prediction due to naphthenic acid and sulfidic corrosion and identify potential hot spots, and supports analytics to prevent potential problems at hot spots in processing units by enabling planning and scheduling teams to quantify corrosion and optimize crude slates.

Figure 1:
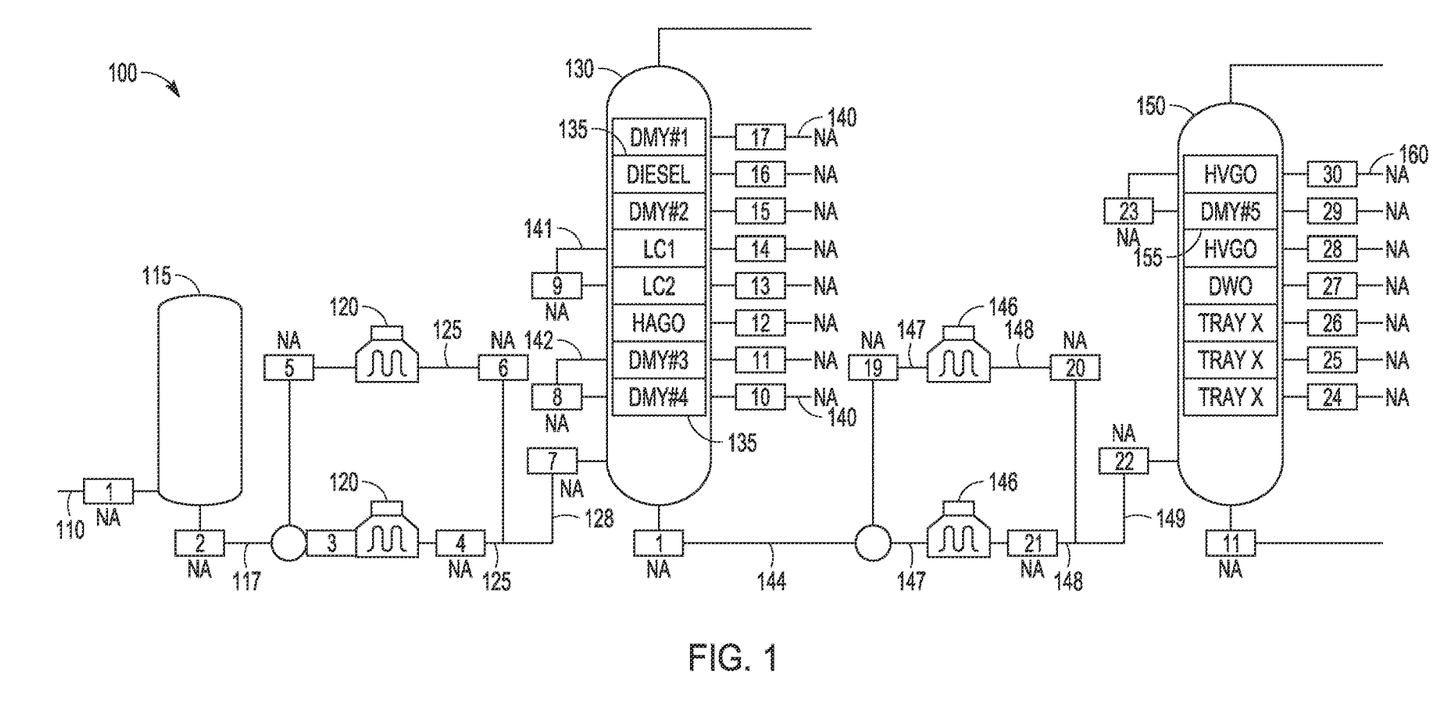
FIG. 1 is a block diagram of a simplified feedstock processing unit according to an example embodiment.

FIG. 1 is a block diagram of a simplified feedstock processing unit 100. Processing unit 100 includes an inlet 110, referred to as a flash drum feed transfer line, to a flash vessel 115 that operates to heat the feedstock to a specified temperature, such as 450 F. The inlet 110 is used to selectively receive different feedstock, such as crude opportunities and blends, under the control of an operator. An outlet 117, referred to as outlet of flash drum, transfers the flash vessel processed feedstock to one or more heaters 120.

Feedstock processed by the heaters 120 is provided via outlets 125 and transfer line 128 to a first distillation tower 130 that includes multiple trays 135. Trays 135 are vertically spaced and are positioned to accumulate fractions of the feedstock condensed at different levels based on a temperature gradient within tower 130. Each tray has an associated side cut line 140 to transfer respective condensed feedstock, such as automotive gas oil (AGO), heavy diesel, medium diesel, light diesel, kerosene, and Naphtha to name a few. Eight trays and corresponding transfer lines are illustrated as an example. More or fewer trays may be used in further embodiments. A dummy draw-off line 141 and LC draw-off line 142 are also shown.

A further outlet 144 transfers remaining feedstock, such as a reduced crude, to further heaters 146. Each heater 146 has an inlet 147 and an outlet 148. The outlets are coupled to transfer the feedstock via transfer line 149 to a vacuum distillation tower 150, which also includes multiple trays 155 and side cut lines 160, seven of which are shown as an example. Example trays collect wash oils, heavy vacuum gas oil (HVGO), medium vacuum gas oil (MVGO), light vacuum gas oil (LVGO), etc.

Note that there may be many more pieces of equipment in processing unit 100, such as pumps, heat exchangers and more to further process the feedstock. The complexity of such processing units makes it extremely complex to determine corrosion rates, much less keep track of the process parameters and metallurgical makeup of each piece of equipment that are involved in estimating resulting corrosion of processing a single crude opportunity.

Figure 2:
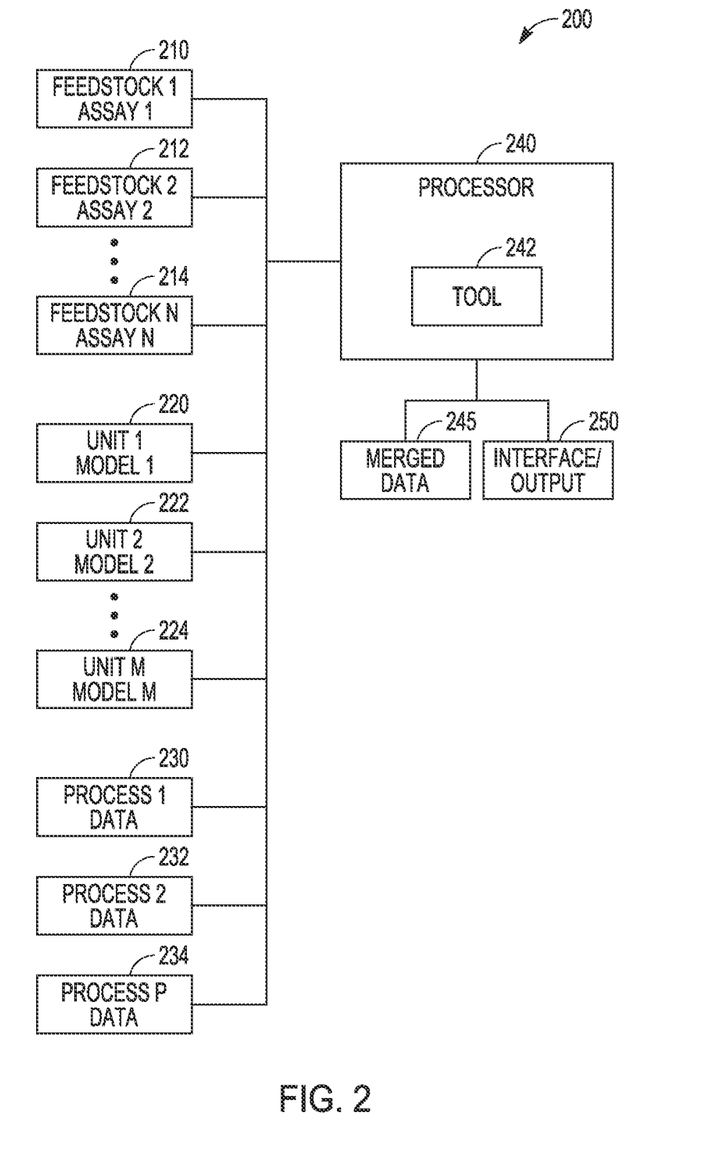
FIG. 2 is a block diagram of a feedstock processing corrosion management system for enabling operators to make informed decisions regarding accepting and processing available feedstocks according to an example embodiment.

FIG. 2 is a block diagram of a feedstock processing corrosion management system 200 for enabling operators to make informed decisions regarding accepting and processing available feedstocks 1-N indicated at 210, 212, and 214. Feedstocks 21, 212, and 214 each have an associated respective assay 1, assay 2, and assay N. Multiple units 1-M indicated at 220, 222, and 224 are available for processing one or more of the feedstocks. The multiple units may be located at a single site, such as a refinery in the case of the feedstock being crude oil or distributed between one or more locations being managed by an operator. Process data 1-P is indicated at 230, 232, and 234. The process data is associated with each of the respective units, or different types of feedstock in different embodiments, but specifies different operating temperature and processing times or throughput rates for processing the feedstock through different units.

In various embodiments, each of the assay, unit model, and process data are typically stored in disparate databases with different schema. System 200 includes a processor 240 used to access the disparate databases and to populate one or more instances of a corrosion rate calculating tool 242. The merged data is stored at 245 and is accessed by the tool 242. The tool 242 also provides an interface 250 to the merged data that includes an output to provide a visualization of the merged data and reports to facilitate selection of opportunity feedstocks to process.

In one example, the corrosion rates are calculated via tool 242 based on the merged data 245. For each unit, each piece of equipment is analyzed via tool 242 based on the metallurgical properties of the equipment, the assay data, and the process data to determine how long, and at what temperature the equipment will be exposed to the feedstock. Corrosion rate is calculated from the weight loss of the metallurgy of the equipment during a corrosion test and has the units of weight loss per unit area per unit time. From most desirable engineering standpoint, corrosion rate is expressed us units of linear units of thickness loss per unit time.

Figure 3:
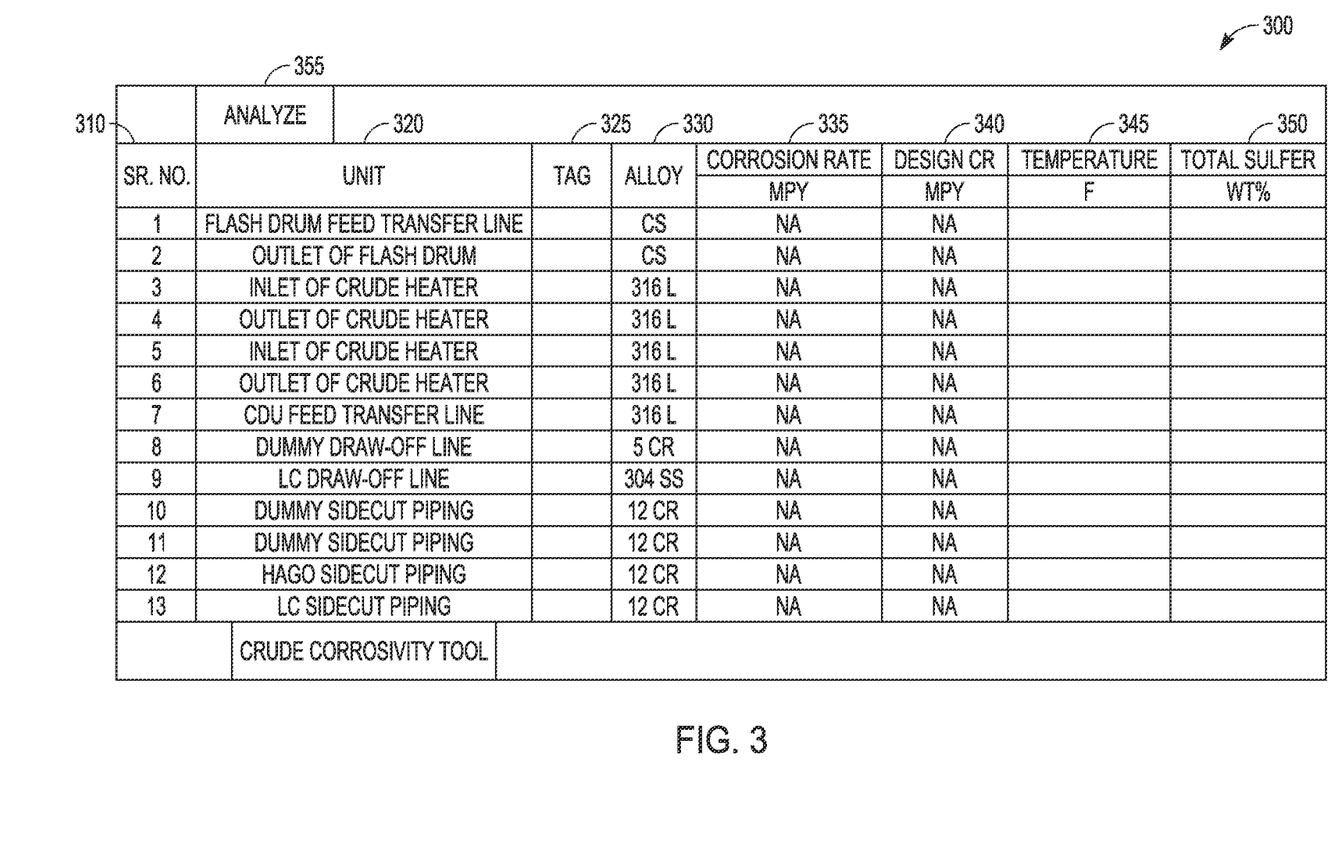
FIG. 3 is a simplified interface including data used to determine corrosion rates for a processing unit according to an example embodiment.

FIG. 3 is a simplified interface 300 including data used to determine corrosion rates for a processing unit, such as unit 100. Interface 300 includes a table 310, such as a spreadsheet in a spreadsheet application, having data derived based on a model of processing unit 100. In one embodiment, interface 300 is provided via tool 242 executing on each unit for each feedstock opportunity. Note that a sequence of numbers starting from 1 are shown in FIG. 1 to reference rows in table 310 containing data related to processing equipment at the point of such sequence of numbers in FIG. 1.

Each row (1-13 of many is visible in the current view with further visible via scrolling) in interface 300 includes a unit column 320, tag column 325, allow column 330, corrosion rate (CR) column 335, design CR column 340 a temperature column 345, and a total sulfur column 350. Also included is an analyze button 355. Each of the columns is designed to hold information relevant for calculating the corrosion rate in column 335 for each piece of processing equipment in unit 100.

The rows in one embodiment are generated based on a logical model of each unit that is to be considered for various opportunity crudes. The model may be similar to that shown in FIG. 1. Note that some of the information is lacking from columns. In a prior interface, values for columns lacking such information were filled in manually.

In one embodiment, the missing information is provided by obtaining assay data for a particular feedstock opportunity, and processing data that specifies at least temperature information for the feedstock during processing by each piece of equipment. There may be multiple instances of the interface, one for each unit, or all the units may be included in sequence. Assay data for each opportunity feedstock is obtained and used to automatically merge corrosivity data to fill in columns relating to acid/sulfur content of each feedstock opportunity. Process data is also obtained and includes processing temperatures and lengths of time needed to process each opportunity feedstock. The process data is also merged into the table 310 to complete the table with all the data needed to calculate the corrosion rate in column 335 using the tool 242.

Figure 4:
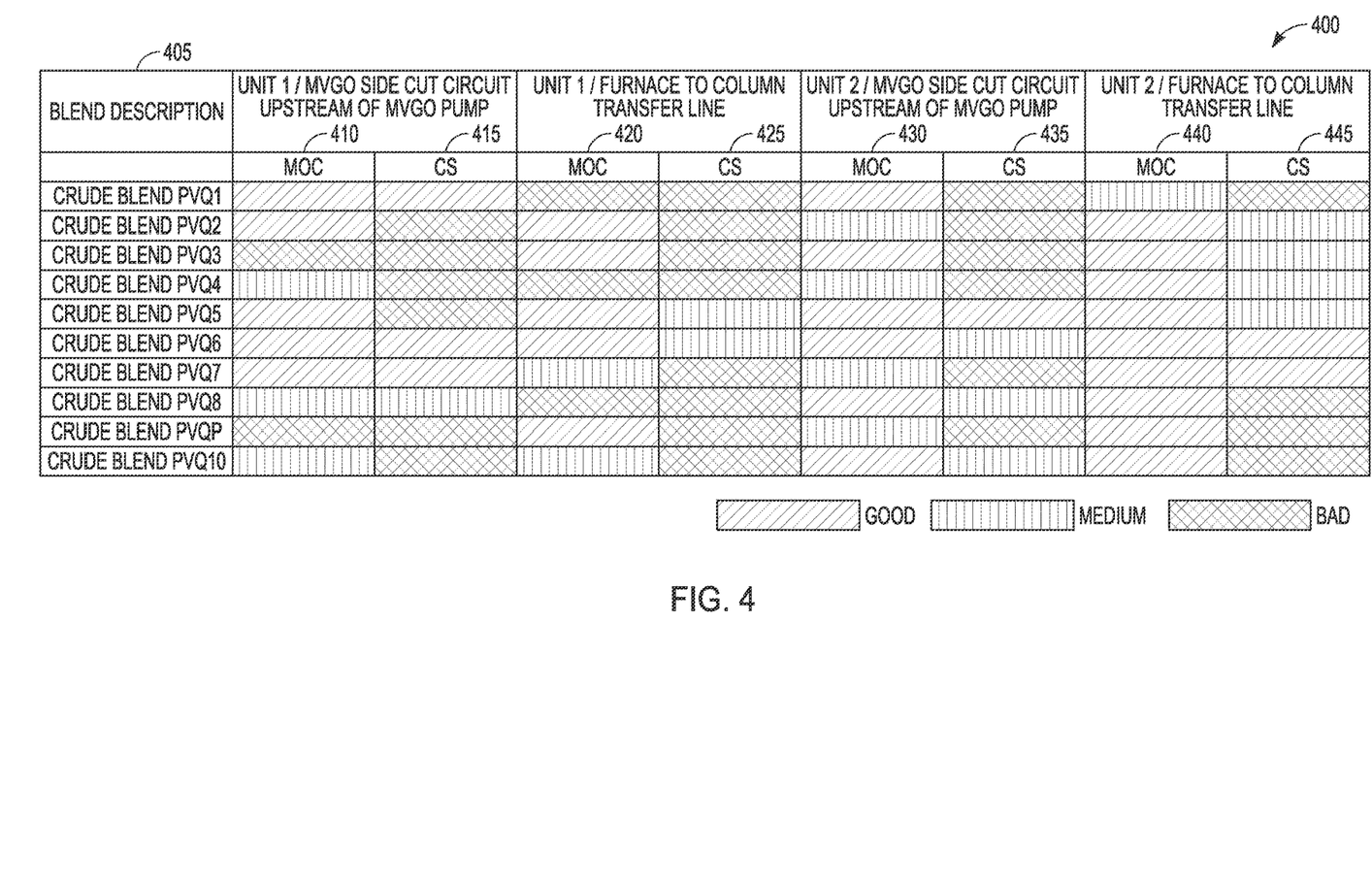
FIG. 4 is a block diagram of an example output showing a crude corrosivity assessment matrix according to an example embodiment.

FIG. 4 is a block diagram of an example output 400 showing a crude corrosivity assessment matrix that is generated by the tool 242 from the merged data 245. A column 405 corresponds to feedstock opportunities, in this case various crude oil blends. Each row corresponds to one of the blends, with the first row corresponding to crude blend PVQ1. Successive rows are labeled PVQ2-10, illustrating corrosivity assessments for ten different blends.

Various corrosivity assessments for multiple units for each crude blend are shown in the columns. Columns 410 and 415 represent a first unit, unit1, side cut circuit that is upstream of an MVGO pump. Each cell in these columns, and the remaining columns may be color coded, with green indicating low corrosivity as illustrated without color in the first row cells in columns 410 and 415. Column 410 corresponds to material of construction (MOC) of the unit1 MVGO side cut circuit upstream of the MVGO pump. Col 415 corresponds to carbon steel (CS) of the same equipment.

Columns 420 and 425 relate to the first unit's furnace to column transfer line illustrating MOC and CS respectively. The first row of such columns is red, corresponding to a high corrosivity assessment.

Columns 430, 435, 440, and 445 correspond MOC and CS of two different pieces of equipment in a second unit, Unit2. For ease of illustration, only two pieces of equipment for each unit, and only two units are shown. In an average application, there may be many more pieces of equipment for each unit and several units, further illustrating the complexity of decision making.

Columns 430 and 435 illustrate MOC and CS of HVGO side cut circuit D/S of and HVGO pump in Unit2, and columns 440 and 445 correspond to MOC and CS of a furnace to column inlet in Unit2. Note that in the first row, the corrosivity assessments vary from good (green) in Column 430 to medium (yellow) in column 440, to bad (red) in columns 435 and 445. These columns include corrosivity assessments for each of the crude blends in the various rows, providing an easy to view and understand corrosivity assessment for each crude, allowing an operator to visually observe corrosivity assessments for multiple units and equipment in each unit for multiple different crudes.

Figure 5:
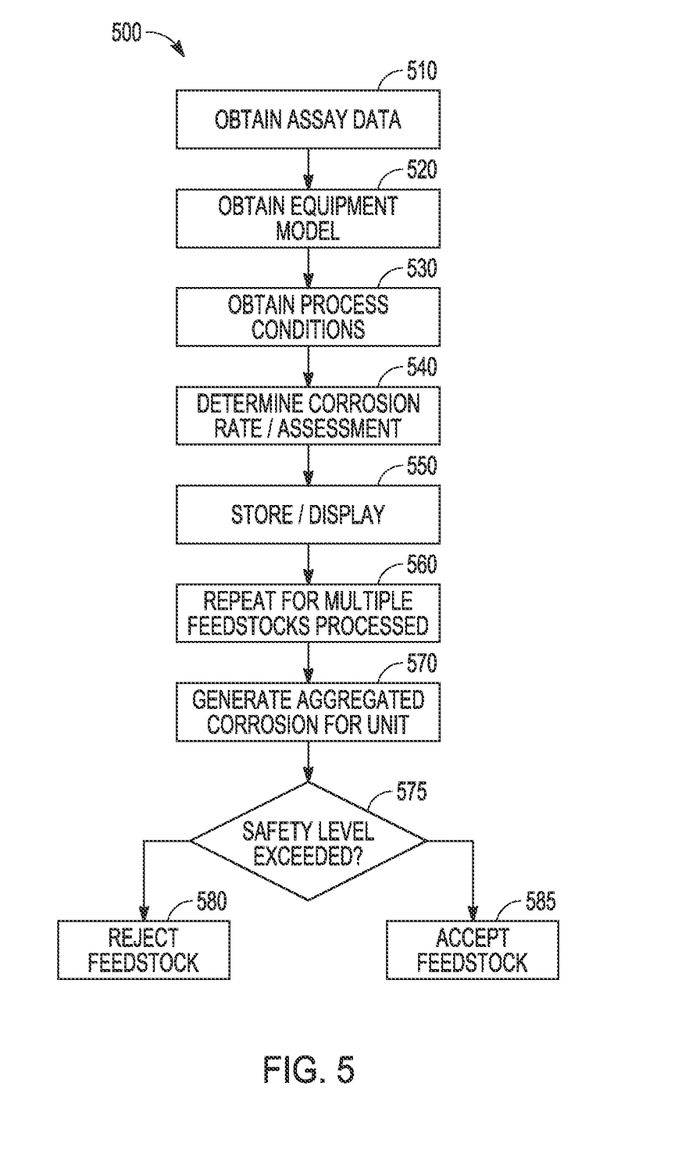
FIG. 5 is a flowchart illustrating a computer implemented method of determining a corrosion amount of a particular feedstock to be processed by a particular processing unit under a first processing condition according to an example embodiment.

FIG. 5 is a flowchart illustrating a computer implemented method 500 of determining a corrosion amount of a particular feedstock to be processed by a particular processing unit under a first processing condition. Method 500 includes operation 510 that obtains, by the computer, assay data for a first feedstock. The assay data contains measurements for one or more aspects of the first feedstock. A first equipment model is obtained at operation 520. The first equipment model contains one or more properties of one or more processing units. Example models may include process flow diagrams (PFD) and piping and instrumentation diagrams in various embodiments.

At operation 530, the computer obtains first processing conditions. The first processing conditions contain one or more variables by which the first feedstock will be processed by the one or more processing units. A first corrosion amount of the one or more processing units is determined at operation 540. The corrosion amount is determined using the first processing conditions, the properties of the one or more processing units contained in the first equipment model and the assay data for the first feedstock. Method 500 continues at operation 550 to store or display the first corrosion amount of the one or more processing units. The first corrosion amount may be both stored and displayed in some embodiments and may be displayed as a corrosivity assessment. The display may be in the form of a color coded or otherwise delineated spreadsheet format in some embodiments, with the color in each cell of the table or spreadsheet indicative of low, medium, or high corrosivity.

In one embodiment, historic corrosion levels are maintained for each processing unit. At operation 560, a second corrosion amount of the one or processing units is determined for a second feedstock. The second corrosion amount comprising an actual or estimated existing corrosion amount of the one or more processing units. Operation 560 is repeated for multiple feedstocks that have been or will be processed by a unit to generate an aggregated corrosion amount or corrosivity assessment for use in one or more of equipment maintenance and other decisions regarding feedstock opportunities.

The aggregated corrosion amount or corrosivity assessment is used to evaluate or determine historic corrosion level for the processing unit. Such determination may be used to determine if a predicted corrosion amount for a new feedstock will exceed a safety threshold prior to processing the feedstock or prior to determining whether or not to accept a new feedstock for processing.

Method 500 in one embodiment uses the aggregated corrosion information to determine at decision operation 575 that a second corrosion amount in conjunction with the first corrosion amount of the one or more processing units exceeds a predetermined safety level. Safety levels may be prescribed by the processing unit manufacturer, a government entity, a process engineer, an operator, or other entity. The safety level may be a physical amount of corrosion of the processing unit measured in metal thickness or a percentage thickness of the original metal thickness of the processing unit for the one or more processing units.

In accordance with a determination at operation 575 that the second corrosion amount for the one or more processing units in conjunction with the first corrosion amount of the one or more processing units exceeds a predetermined safety level for the one or more processing units, a warning is displayed at operation 580, such as a safety warning that processing the first feedstock with the first equipment model and the stored corrosion amount under the processing conditions will cause a new corrosion amount that in conjunction with the stored corrosion amount will cause unacceptable corrosion to the processing unit. The warning may be interpreted as an indication that the second feedstock should be rejected and not processed.

In accordance with a determination at operation 575 that the second corrosion amount in conjunction with the first corrosion amount does not exceed safety levels, an indication that it is safe is generated at operation 585 indicative of an indication that the feedstock may be accepted. The indication may be a display that second corrosion amount is acceptable can be a color coding, such as green, a text output the new predicted total amount of corrosion, or other indication.

In some embodiments, multiple corrosion amounts corresponding to the processing of multiple feedstocks are determined. An aggregate corrosion amount may be determined based on each prior determined corrosion amount in conjunction with each other. The aggregate corrosion amount in the case of two prior corrosion amounts, the first and second corrosion amounts, may be called a third corrosion amount and may be stored as a new historic corrosion level for the processing unit.

In one embodiment, the third corrosion amount of the one or more processing units may replace the second corrosion amount or may be stored separately so historic corrosion levels for the processing unit are tracked. If stored separately, an indication is made that for future corrosion calculations, the latest total corrosion amount should be used to account for past corrosion.

Figure 6:
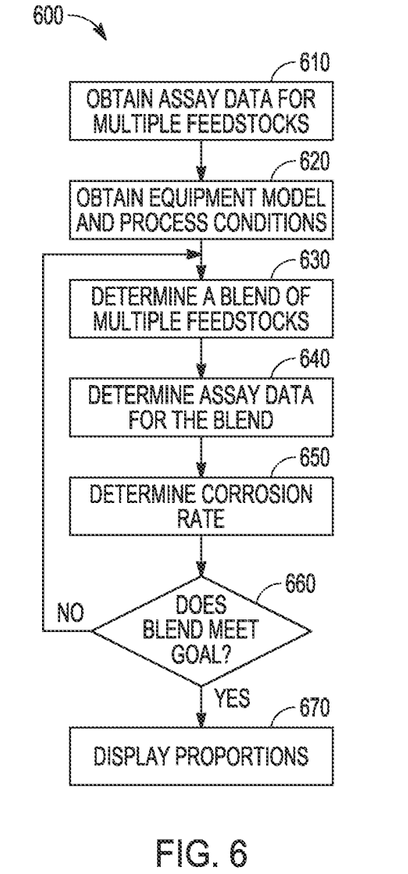
FIG. 6 is a flowchart illustrating a computer implemented method of determining combinations of feedstock blends to satisfy a goal according to an example embodiment.

FIG. 6 is a flowchart illustrating a computer implemented method 600 of determining combinations of feedstocks, commonly referred to as blends, such as crude oil opportunity blends to satisfy a goal. At operation 610, assay data for multiple feedstocks is obtained. The assay data contains measurements for one or more aspects of the multiple feedstocks, one or more of which may have already been obtained and ready for use, and one or more of which may be available to be obtained. At operation 620, an equipment model and process conditions are obtained. A possible blend of two or more of the blends is determined at operation 630. The blend may be determined by simply adding two or more of the feedstocks, such as one that is already obtained, and one that is available to be obtained. The possible blend may also be various combinations of ready to use and/or available to be obtained feedstocks.

Once the possible blend is determined, at operation 640, the assay data for the possible blend is determined. The assay data is simply a volume weighted average of the assay data for each feedstock comprising the possible blend in one embodiment. In further embodiments, more complex calculations may be performed to arrive at the blend assay data based on empirical experiments or other means of determine the blend assay data.

At operation 650, a corrosion amount of the one or more processing units is determined using the processing conditions, the equipment model, and the assay data for the determined blend of the feedstocks.

Once the corrosion amount is determined at operation 650, processing proceeds to a decision operation 660. Decision operation 660 is used to determine whether or not certain goals are met. If the goal is not met as indicated by NO, processing proceeds back to operation 630 to determine a new possible blend to repeat operations to determine a new corrosion amount and return again to decision operation 660, creating a loop. The loop is executed until a goal is met as indicated by YES, wherein operation 670 is performed to display proportions of each feedstock that comprise the blend whose corrosion amount met the goal at decision operation 660.

During execution of the loop, the proportions of each feedstock may be iteratively modified by a selected amount in one embodiment. For instance, a blend may start at 10 percent of a first feedstock and 90 percent of a second feedstock. The next iterations may be changed in 5 percent increments. For instance, the next iteration may comprise a blend of 15 percent of the first feedstock and 85 percent of the second feedstock. A record of each blend proportion is saved, and compared to the goal, with the proportions best meeting the goal being selected for display at operation 670. In further embodiments, iterations may stop if the results are moving further away from the goal. In still further embodiments, an operator may select increments, starting proportions, or may also select proportions for one or more iterations.

One goal at operation 660 is to minimize the first corrosion amount of the one or more processing units when the determined blend is processed using the processing conditions, the equipment model and the assay data for the blend of the feedstocks. In a further embodiment, the goal is to optimize profit that may be obtained. In one example, the first feedstock is associated with a first market price and the second feedstock is associated with a second market price. The first proportion of the first feedstock and the first proportion of the second feedstock to minimize a first price of the determined blend, the first price of the determined blend based on the first market price of the first proportion of the first feedstock and the second market price of the first proportion of the second feedstock, when the determined blend is processed.

In one embodiment the goal at operation 660 is directed toward maximizing profit while minimizing corrosion. Again, the first feedstock is associated with a first market price and the second feedstock is associated with a second market price, and the loop is used to determine the first proportion of the first feedstock and the first proportion of the second feedstock to minimize a first price of the determined blend and the first corrosion amount of the one or more processing units. The first price of the determined blend is based on the first market price of the first proportion of the first feedstock and the second market price of the first proportion of the second feedstock. At operation 670, in response to the determined blend is processed using the first processing conditions, the first equipment model and the assay data for the blend of the first feedstock and the second feedstock, the feedstock proportions are displayed or otherwise provided to an operator.

Figure 7:
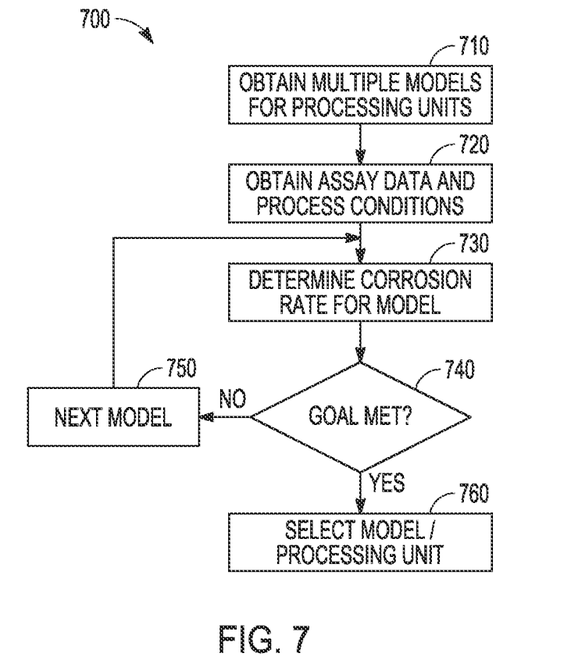
FIG. 7 is a flowchart illustrating a computer implemented method for selecting an equipment model corresponding to a processing unit based on a selected goal according to an example embodiment.

FIG. 7 is a flowchart illustrating a computer implemented method 700 for selecting an equipment model corresponding to a processing unit based on a selected goal. Method 700 begins with operation 710 by obtaining multiple models of various processing units. The models are equipment models that contain one or more properties of equipment in one or more associated processing units. At operation 720, assay data for a feedstock and process condition for processing the feedstock are obtained.

Method 700 determines a corrosion amount at operation 730 for an equipment model. The corrosion amount is determined using the obtained processing conditions, the properties of the processing unit contained in the corresponding equipment model, and the assay data for the feedstock. At a decision operation 740, a comparison of the corrosion amount is made to a selected goal. In response to the goal not being met as indicated by NO, processing continues to operation 750 to select a next model for which to determine the corrosion amount at operation 730 and determine if the goal is met at decision operation 740, forming a processing loop.

In one embodiment, the processing loop continues until the goal is met as indicated by YES, whereupon the model corresponding a processing unit is selected at 760.

The goal in one embodiment is based on the corrosion amount being the smallest. The loop in this embodiment basically continues until all models are processed, whereupon decision operation 740 determines the model exhibiting the smallest corrosion amount.

In further embodiments, the decision operation 740 may test for one or more of goals comprising selecting the equipment model to maximize profit, selecting the processing conditions, such as time for processing one or more feedstocks, to minimize corrosion, selecting the processing conditions and feedstock to maximize profit, and selecting the processing conditions to maximize throughput. One example may include selecting a smaller volume of highly corrosive feedstock that becomes available that can be processed in a relative short time period. The short period of time to process the highly corrosive feedstock limits the corrosive effects on the processing units. A current feedstock's processing may even be interrupted for such a smaller volume and then continued later.

Figure 8:
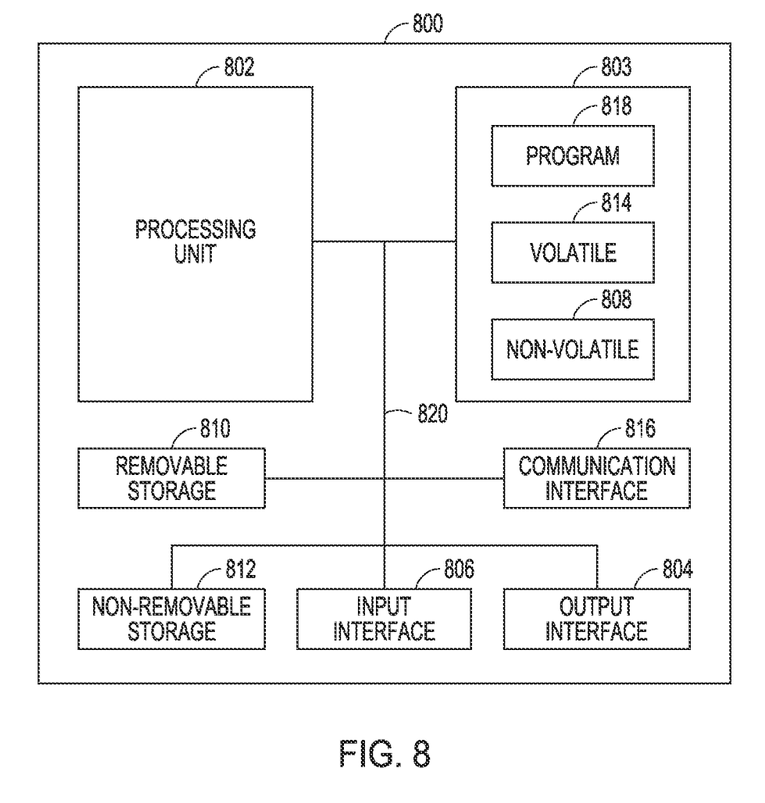
FIG. 8 is a block schematic diagram of a computer system to perform feedstock processing corrosion management functions according to an example embodiment.

FIG. 8 is a block schematic diagram of a computer system 800 to perform feedstock processing corrosion management functions according to example embodiments. All components need not be used in various embodiments.

One example computing device in the form of a computer 800 may include a processing unit 802, memory 803, removable storage 810, and non-removable storage 812. Although the example computing device is illustrated and described as computer 800, the computing device may be in different forms in different embodiments. For example, the computing device may instead be a smartphone, a tablet, smartwatch, smart storage device (SSD), or other computing device including the same or similar elements as illustrated and described with regard to FIG. 8. Devices, such as smartphones, tablets, and smartwatches, are generally collectively referred to as mobile devices or user equipment.

Although the various data storage elements are illustrated as part of the computer 800, the storage may also or alternatively include cloud-based storage accessible via a network, such as the Internet or server based storage. Note also that an SSD may include a processor on which the parser may be run, allowing transfer of parsed, filtered data through I/O channels between the SSD and main memory.

Memory 803 may include volatile memory 814 and non-volatile memory 808. Computer 800 may include—or have access to a computing environment that includes—a variety of computer-readable media, such as volatile memory 814 and non-volatile memory 808, removable storage 810 and non-removable storage 812. Computer storage includes random access memory (RAM), read only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 800 may include or have access to a computing environment that includes input interface 806, output interface 804, and a communication interface 816. Output interface 804 may include a display device, such as a touchscreen, that also may serve as an input device. The input interface 806 may include one or more of a touchscreen, touchpad, mouse, keyboard, camera, one or more device-specific buttons, one or more sensors integrated within or coupled via wired or wireless data connections to the computer 800, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer 800 are connected with a system bus 820.

Computer-readable instructions stored on a computer-readable medium are executable by the processing unit 802 of the computer 800, such as a program 818. The program 818 in some embodiments comprises software to implement one or more method described herein. A hard drive, CD-ROM, and RAM are some examples of articles including a non-transitory computer-readable medium such as a storage device. The terms computer-readable medium and storage device do not include carrier waves to the extent carrier waves are deemed transitory. Storage can also include networked storage, such as a storage area network (SAN). Computer program 818 along with the workspace manager 822 may be used to cause processing unit 802 to perform one or more methods or algorithms described herein.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A computer-implemented method comprising:
obtaining, by a computer, assay data for a first feedstock, the assay data containing measurements for one or more aspects of the first feedstock;
obtaining, by the computer, a first equipment model, the first equipment model containing one or more properties of one or more processing units;
obtaining, by the computer, first processing conditions, the first processing conditions containing one or more variables by which the first feedstock will be processed by the one or more processing units;
determining, by the computer, a first corrosion amount of the one or more processing units using the first processing conditions, the one or more properties of the one or more processing units contained in the first equipment model, and the assay data for the first feedstock;
obtaining, by the computer, assay data for a second feedstock, the assay data containing measurements for one or more aspects of the second feedstock;
determining, by the computer, a blend of the first feedstock and a second feedstock, wherein the determined blend is based on a first proportion of the first feedstock and a first proportion of the second feedstock;
determining, by the computer, the first proportion of the first feedstock and the first proportion of the second feedstock to reduce the first corrosion amount of the one or more processing units when the determined blend is processed using the first processing conditions, the first equipment model, and the assay data for the blend of the first feedstock and the second feedstock;
determining, by the computer, assay data for the blend of the first feedstock and the second feedstock, wherein the determination of the first corrosion amount of the one or more processing units is further determined using the assay data for the determined blend of the first feedstock and the second feedstock;
displaying, by the computer, on at least one display:
the first corrosion amount of the one or more processing units, the first proportion of the first feedstock, and the first proportion of the second feedstock; and
a corrosivity assessment matrix comprising at least one entry, wherein the at least one entry comprises (i) an identifier for the blend of the first feedstock and the second feedstock and (ii) a corrosivity assessment rendered in one of a plurality of colors based on the first corrosion amount;
controlling, by the computer, blending of the first feedstock and the second feedstock in the corresponding first proportion to obtain the blend of the first feedstock and the second feedstock; and
causing, by the computer, processing of the blend using the one or more processing units to obtain one or more condensed feedstocks.

2. The method of claim 1, wherein the one or more properties of the one or more processing units comprise a second corrosion amount of the one or processing units, the second corrosion amount comprising an actual or estimated existing corrosion amount of the one or more processing units.

3. The method of claim 2, further comprising:
obtaining, by the computer, the second corrosion amount of the one or more processing units; and determining, by the computer, whether the second corrosion amount for the one or more processing units in conjunction with the first corrosion amount of the one or more processing units exceeds a predetermined safety level for the one or more processing units; and in accordance with a determination that the second corrosion amount for the one or more processing units in conjunction with the first corrosion amount of the one or more processing units exceeds a predetermined safety level for the one or more processing units, displaying, by the computer, a safety warning on the at least one display.

4. The method of claim 2, further comprising:

obtaining, by the computer, the second corrosion amount of the one or more processing units;

determining, by the computer, a third corrosion amount of the one or more processing units, the third corrosion amount comprising the first corrosion amount for the one or more processing units in conjunction with the second corrosion amount for the one or more processing units; and storing, by the computer, the third corrosion amount of the one or more processing units.

5. The method of claim 2, further comprising:

obtaining, by the computer, the second corrosion amount of the one or more processing units;

determining, by the computer, whether the second corrosion amount for the one or more processing units in conjunction with the first corrosion amount of the one or more processing units exceeds a predetermined safety level for the one or more processing units; and in accordance with a determination that the second corrosion amount for the one or more processing units in conjunction with the first corrosion amount of the one or more processing units does not exceed a predetermined safety level for the one or more processing units, displaying, by the computer, an indication on the at least one display, wherein the indication indicates that the second corrosion amount for the one or more processing units in conjunction with the first corrosion amount of the one or more processing units is acceptable.

6. The method of claim 1, wherein:

the first feedstock is associated with a first market price and the second feedstock is associated with a second market price; and the method further comprises:

determining, by the computer, the first proportion of the first feedstock and the first proportion of the second feedstock to minimize a first price of the determined blend, the first price of the determined blend based on the first market price of the first proportion of the first feedstock and the second market price of the first proportion of the second feedstock, when the determined blend is processed using the first processing conditions, the first equipment model and the assay data for the blend of the first feedstock and the second feedstock; and displaying, by the computer, the determined first proportion of the first feedstock and the first proportion of the second feedstock on at least one display.

7. The method of claim 1, wherein the first feedstock is associated with a first market price and the second feedstock is associated with a second market price, and the method further comprises:

determining, by the computer, the first proportion of the first feedstock and the first proportion of the second feedstock to minimize a first price of the determined blend and the first corrosion amount of the one or more processing units, the first price of the determined blend based on the first market price of the first proportion of the first feedstock and the second market price of the first proportion of the second feedstock, when the determined blend is processed using the first processing conditions, the first equipment model and the assay data for the blend of the first feedstock and the second feedstock; and displaying, by the computer, the determined first proportion of the first feedstock and the first proportion of the second feedstock on at least one display.

8. The method of claim 1, further comprising:

accessing, by the computer, a plurality of equipment models, each of the plurality of equipment models containing one or more properties of one or more associated processing units;

determining, by the computer, for each of a plurality of equipment models, the first corrosion amount of the one or more associated processing units, the corrosion amount determined using the first processing conditions, the one or more properties of the one or more associated processing units contained in each of the plurality of equipment models and the assay data for the first feedstock; and selecting, by the computer, the first equipment model from one or more equipment models; wherein the selected first equipment model is the equipment model of the plurality of equipment models for which the determined first corrosion amount is the smallest.

9. The method of claim 1 wherein at least one of the first feedstock or the second feedstock comprises a shipment of crude oil and wherein the first equipment model comprises a model of crude oil processing equipment.

10. One or more non-transitory, computer-readable storage media including instructions that, when executed by one or more processors, cause the one or more processors to:

obtain assay data for a first feedstock, the assay data containing measurements for one or more aspects of the first feedstock;

obtain a first equipment model, the first equipment model containing one or more properties of one or more processing units;

obtain first processing conditions, the first processing conditions containing one or more variables by which the first feedstock will be processed by the one or more processing units;

determine a first corrosion amount of the one or more processing units, the corrosion amount determined using the first processing conditions, the one or more properties of the one or more processing units contained in the first equipment model and the assay data for the first feedstock;

obtain assay data for a second feedstock, the assay data containing measurements for one or more aspects of the second feedstock;

determine a blend of the first feedstock and a second feedstock, wherein the determined blend is based on a first proportion of the first feedstock and a first proportion of the second feedstock;

determine the first proportion of the first feedstock and the first proportion of the second feedstock to reduce the first corrosion amount of the one or more processing units when the determined blend is processed using the first processing conditions, the first equipment model, and the assay data for the blend of the first feedstock and the second feedstock;

determine assay data for the blend of the first feedstock and the second feedstock, wherein the determination of the first corrosion amount of the one or more processing units is further determined using the assay data for the determined blend of the first feedstock and the second feedstock;

display, on at least one display:
the first corrosion amount of the one or more processing units, the first proportion of the first feedstock, and the first proportion of the second feedstock; and
a corrosivity assessment matrix comprising at least one entry, wherein the at least one entry comprises (i) an identifier for the blend of the first feedstock and the second feedstock and (ii) a corrosivity assessment rendered in one of a plurality of colors based on the first corrosion amount;

control blending of the first feedstock and the second feedstock in the corresponding first proportion to obtain the blend of the first feedstock and the second feedstock; and cause processing of the blend using the one or more processing units to obtain one or more condensed feedstocks.

11. The one or more non-transitory, computer-readable storage media of claim 10, wherein the one or more properties of the one or more processing units comprise a second corrosion amount of the one or processing units, the second corrosion amount comprising an actual or estimated existing corrosion amount of the one or more processing units, and wherein the instructions, when executed by the one or more processors, further cause the one or more processors to:
obtain the second corrosion amount of the one or more processing units; and
determine whether the second corrosion amount for the one or more processing units in conjunction with the first corrosion amount of the one or more processing units exceeds a predetermined safety level for the one or more processing units; and
in accordance with a determination that the second corrosion amount for the one or more processing units in conjunction with the first corrosion amount of the one or more processing units exceeds a predetermined safety level for the one or more processing units, display a safety warning on the at least one display.

12. The one or more non-transitory, computer-readable storage media of claim 10, wherein the one or more properties of the one or more processing units comprise a second corrosion amount of the one or processing units, the second corrosion amount comprising an actual or estimated existing corrosion amount of the one or more processing units, and wherein the instructions, when executed by the one or more processors, further cause the one or more processors to:
obtain the second corrosion amount of the one or more processing units;
determine a third corrosion amount of the one or more processing units, the third corrosion amount comprising the first corrosion amount for the one or more processing units in conjunction with the second corrosion amount for the one or more processing units; and
store the third corrosion amount of the one or more processing units.

13. The one or more non-transitory, computer-readable storage media of claim 10, wherein the one or more properties of the one or more processing units comprise a second corrosion amount of the one or processing units, the second corrosion amount comprising an actual or estimated existing corrosion amount of the one or more processing units, and wherein the instructions, when executed by the one or more processors, further cause the one processors to:
obtain the second corrosion amount of the one or more processing units;
determine whether the second corrosion amount for the one or more processing units in conjunction with the first corrosion amount of the one or more processing units exceeds a predetermined safety level for the one or more processing units; and
in accordance with a determination that the second corrosion amount for the one or more processing units in conjunction with the first corrosion amount of the one or more processing units does not exceed a predetermined safety level for the one or more processing units, display, on the at least one display, an indication that the second corrosion amount for the one or more processing units in conjunction with the first corrosion amount of the one or more processing units is acceptable.

14. The one or more non-transitory, computer-readable storage media of claim 10, wherein:
the first feedstock is associated with a first market price and the second feedstock is associated with a second market price; and
the instructions, when executed by the one or more processors, further cause the one or more processors to:
determine the first proportion of the first feedstock and the first proportion of the second feedstock to minimize a first price of the determined blend, the first price of the determined blend, the first price of the determined blend based on the first market price of the first proportion of the first feedstock and the second market price of the first proportion of the second feedstock, when the determined blend is processed using the first processing conditions, the first equipment model and the assay data for the blend of the first feedstock and the second feedstock; and
display the determined first proportion of the first feedstock and the first proportion of the second feedstock on the at least one display.

15. The one or more non-transitory, computer-readable storage media of claim 10, wherein the determined blend is based on a first proportion of the first feedstock and a first proportion of the second feedstock and wherein the first feedstock is associated with a first market price and the second feedstock is associated with a second market price, and the instructions, when executed by the one or more processors, further cause the one or more processors to:
determine the first proportion of the first feedstock and the first proportion of the second feedstock to minimize a first price of the determined blend and the first corrosion amount of the one or more processing units, the first price of the determined blend based on the first market price of the first proportion of the first feedstock and the second market price of the first proportion of the second feedstock, when the determined blend is processed using the first processing conditions, the first equipment model and the assay data for the blend of the first feedstock and the second feedstock.

16. The method of claim 1, wherein:
determining the first proportion of the first feedstock and the first proportion of the second feedstock, comprises:

iteratively generating a corrosion amount for each of a plurality of proportion combinations of the first feedstock and the second feedstock in the blend using the assay data for the first feedstock, the assay data for the second feedstock, the first processing conditions, and the first equipment model, wherein the first proportion of the first feedstock and the first proportion of the second feedstock are determined based on one of the plurality of proportion combinations associated with a lowest value for the corrosion amount.

17. The method of claim 16, wherein:
the at least one entry of the corrosivity assessment matrix comprises a plurality of entries, wherein each of the plurality of entries comprises:
   a respective identifier for one of the plurality of proportion combinations of the first feedstock and the second feedstock in the blend; and
   a corrosivity assessment rendered in one of the plurality of colors based on the corrosion amount associated with the one of the plurality of proportion combinations.

18. The method of claim 1, wherein:
the one or more processing units comprise a plurality of processing units;
the first equipment model contains one or more properties of each processing unit of the plurality of processing units;
the method further comprises:
   determining a respective corrosion amount for the plurality of processing units based on the assay data for the determined blend of the first feedstock and the second feedstock, the first processing conditions, and the one or more properties of the respective processing unit contained in the first equipment model; and
the at least one the corrosivity assessment matrix comprises a respective corrosivity assessment for each of the plurality of processing units, wherein the respective corrosivity assessment is rendered in one of the plurality of colors based on the corresponding corrosion amount for the respective processing unit.

19. A system comprising:
at least one display;
a processor; and
a memory device coupled to the processor and having a program stored thereon for execution by the processor to perform operations comprising:
   obtaining, by a computer, assay data for a first feedstock, the assay data containing measurements for one or more aspects of the first feedstock;
   obtaining a first equipment model, the first equipment model containing one or more properties of one or more processing units;
   obtaining first processing conditions, the first processing conditions containing one or more variables by which the first feedstock will be processed by the one or more processing units;
   determining a first corrosion amount of the one or more processing units using the first processing conditions, the one or more properties of the one or more processing units contained in the first equipment model, and the assay data for the first feedstock;
   obtaining assay data for a second feedstock, the assay data containing measurements for one or more aspects of the second feedstock;
   determining a blend of the first feedstock and a second feedstock, wherein the determined blend is based on a first proportion of the first feedstock and a first proportion of the second feedstock;
   determining the first proportion of the first feedstock and the first proportion of the second feedstock to reduce the first corrosion amount of the one or more processing units when the determined blend is processed using the first processing conditions, the first equipment model, and the assay data for the blend of the first feedstock and the second feedstock;
   determining assay data for the blend of the first feedstock and the second feedstock, wherein the determination of the first corrosion amount of the one or more processing units is further determined using the assay data for the determined blend of the first feedstock and the second feedstock;
   displaying on the at least one display:
      the first corrosion amount of the one or more processing units, the first proportion of the first feedstock, and the first proportion of the second feedstock; and
      a corrosivity assessment matrix comprising at least one entry, wherein the at least one entry comprises (i) an identifier for the blend of the first feedstock and the second feedstock and (ii) a corrosivity assessment rendered in one of a plurality of colors based on the first corrosion amount; and
   controlling blending of the first feedstock and the second feedstock in the corresponding first proportion to obtain the blend of the first feedstock and the second feedstock; and
   causing processing of the blend using the one or more processing units to obtain one or more condensed feedstocks.

20. The system of claim 19, further comprising:
the one or more processing units configured to process the blend to obtain the one or more condensed feedstocks.

* * * * *